United States Patent
Deibel et al.

(10) Patent No.: US 8,624,164 B2
(45) Date of Patent: Jan. 7, 2014

(54) SHUT-OFF TIMER FOR A HEATING BLANKET

(75) Inventors: Rudolf A. Deibel, Eden Prairie, MN (US); Scott A. Entenman, St. Paul, MN (US); Keith J. Leland, Medina, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 1298 days.

(21) Appl. No.: 12/016,731

(22) Filed: Jan. 18, 2008

(65) Prior Publication Data

US 2008/0173629 A1    Jul. 24, 2008

Related U.S. Application Data

(60) Provisional application No. 60/885,422, filed on Jan. 18, 2007.

(51) Int. Cl.
*H05B 3/00*    (2006.01)

(52) U.S. Cl.
USPC ........... 219/212; 219/217; 219/543; 219/549; 219/527

(58) Field of Classification Search
USPC ......... 219/211, 212, 300, 492, 494, 505, 506, 219/527–529, 531, 535, 548
See application file for complete search history.

(56) References Cited

U.S. PATENT DOCUMENTS

| | | | |
|---|---|---|---|
| 3,808,403 A | 4/1974 | Kanaya et al. | |
| 3,900,654 A | 8/1975 | Stinger | |
| 3,936,661 A | 2/1976 | Furuishi et al. | |
| 4,061,898 A | 12/1977 | Murray et al. | |
| 4,149,066 A | 4/1979 | Niibe | |
| 4,479,795 A | 10/1984 | Mustacich et al. | |
| 4,534,886 A | 8/1985 | Kraus et al. | |
| 4,626,664 A | 12/1986 | Grise | |
| 4,658,119 A * | 4/1987 | Endo et al. | 219/492 |
| 4,719,335 A | 1/1988 | Batliwalla et al. | |
| 4,764,665 A | 8/1988 | Orban et al. | |
| 4,798,936 A | 1/1989 | Johnson, Sr. | |
| 4,912,306 A | 3/1990 | Grise et al. | |
| 5,008,515 A | 4/1991 | McCormack | |
| 5,010,233 A | 4/1991 | Henschen et al. | |
| 5,023,433 A | 6/1991 | Gordon | |

(Continued)

FOREIGN PATENT DOCUMENTS

GB    586745    3/1947

OTHER PUBLICATIONS

EeonTexTM Conductive Testiles, Product Details, www.eeonyx.com/prodte.html, Sep. 19, 2006, pp. 1-5.

(Continued)

*Primary Examiner* — Brian Jennison
(74) *Attorney, Agent, or Firm* — Fredrikson & Byron, PA (57) ABSTRACT

A blanket for warming patients during surgery and other medical procedures. The blanket includes one or more temperature sensors and a shut-off timer to prevent prolonged exposure of excessive heat to a patient. Embodiments of the present invention provide a safety feature that cuts power to a heating blanket after a certain period of time has elapsed, irrespective of the feedback provided by a temperature sensor concerning the blanket temperature. That period of time is longer than it takes for the blanket to reach its threshold temperature but shorter than it takes to cause thermal burn injury.

29 Claims, 5 Drawing Sheets

(56) References Cited

U.S. PATENT DOCUMENTS

| | | | |
|---|---|---|---|
| 5,380,580 A | 1/1995 | Rogers et al. | |
| 5,422,462 A | 6/1995 | Kishimoto | |
| 5,443,056 A | 8/1995 | Smith et al. | |
| 5,773,275 A | 6/1998 | Anderson et al. | |
| 5,817,145 A | 10/1998 | Augustine et al. | |
| 5,824,996 A | 10/1998 | Kochman et al. | |
| 5,928,274 A | 7/1999 | Augustine | |
| 5,964,792 A | 10/1999 | Augustine | |
| 5,974,605 A | 11/1999 | Dickerhoff et al. | |
| 5,986,243 A | 11/1999 | Campf | |
| 6,078,026 A | 6/2000 | West | |
| 6,093,910 A | 7/2000 | McClintock et al. | |
| 6,147,333 A * | 11/2000 | Mattson | 219/531 |
| 6,172,344 B1 | 1/2001 | Gordon et al. | |
| 6,184,496 B1 | 2/2001 | Pearce | |
| 6,235,049 B1 | 5/2001 | Nazerian | |
| 6,373,034 B1 | 4/2002 | Rock et al. | |
| 6,403,935 B2 | 6/2002 | Kochman et al. | |
| 6,483,087 B2 | 11/2002 | Gardner et al. | |
| 6,582,456 B1 | 6/2003 | Hand et al. | |
| 6,770,848 B2 * | 8/2004 | Haas et al. | 219/212 |
| 6,770,854 B1 | 8/2004 | Keane | |
| 6,839,922 B1 | 1/2005 | Foggett et al. | |
| 6,974,935 B2 | 12/2005 | O'Grady | |
| 7,022,950 B2 | 4/2006 | Haas et al. | |
| 7,053,344 B1 | 5/2006 | Surjan et al. | |
| 7,282,676 B1 * | 10/2007 | Bouchier et al. | 219/497 |
| 2002/0005398 A1 | 1/2002 | Gillner et al. | |
| 2002/0117495 A1 | 8/2002 | Kochman et al. | |
| 2005/0016982 A1 | 1/2005 | Campf et al. | |

OTHER PUBLICATIONS

International Search Report, dated May 23, 2008 for corresponding PCT Application No. PCT/US2008/051443 (2 pages).

* cited by examiner

SHUT-OFF TIMER FOR A HEATING BLANKET

CROSS-REFERENCE TO RELATED APPLICATION

This application claims priority under 35 U.S.C. §119(e) to U.S. provisional application 60/885,422, filed Jan. 18, 2007, which is hereby incorporated by reference in its entirety.

TECHNICAL FIELD

The present invention is related to heating or warming blankets or pads and more particularly to those including electrical heating elements.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic if not warmed.

Several companies have developed electric warming blankets that can be placed over patients during surgery. However, these electric blankets have a number of inadequacies. For example, a patient may suffer thermal burn injury if the blanket is accidentally left in contact with the skin for a prolonged period of time or if a portion of the blanket becomes faulty and overheats.

To prevent blanket overheating, companies have included one or more temperature sensors in a blanket that can sense the temperature in a desired area and then provide feedback to a control system. The temperature sensor can be placed in an area that would be in contact with a patient or in an area that would reflect an average temperature of the blanket. The control system shuts off the power supply and/or triggers an alarm if the sensed temperature is too high. Thus, the temperature sensor acts as a safety feature to help protect patients from blanket overheating.

However, while a temperature sensor can help prevent blanket overheating, additional safety features would be desirable in case the temperature sensor does not reliably report an accurate average temperature of the blanket. This can happen in a number of situations. In some cases, the temperature sensor itself may simply be damaged and may provide false information to the control system. In other cases, the temperature sensed may be cooler than the temperatures of other areas of the blanket. This could occur, for example, if a cool object such as a metal pan or an ice bag is placed on the blanket near the temperature sensor. The cool object acts as a heat sink and absorbs heat from the blanket, causing the area near the sensor to feel cooler. In another example, the area of the blanket near the temperature sensor may become wet or damaged. In each of these examples, the temperature of the blanket in the temperature sensor area is cooler than the temperature of other areas of the blanket. The cool sensed temperature allows the control system to continue supplying power to the blanket, even though the temperatures in the other areas are too high. The other temperatures would continue rising to excessive levels and body parts in contact with these areas of the blanket may suffer thermal burn injury if in contact with the blanket for a prolonged period of time.

Accordingly, there is a need for a blanket that incorporates an additional safety feature other than a temperature sensor. Further, there is a need for a blanket that incorporates a safety feature that prevents a patient from being exposed to excessive heat for a prolonged period of time. Various embodiments of the invention described herein solve one or more of the problems discussed above.

SUMMARY

Embodiments of the present invention provide a safety feature that cuts power to a heating blanket after a certain period of time has elapsed, irrespective of the feedback provided by a temperature sensor concerning the blanket temperature. That period of time is longer than it takes for the blanket to reach its threshold temperature but shorter than it takes to cause thermal burn injury.

In a first aspect, the present invention provides an electric warming blanket for warming patients during surgery and other medical procedures. The blanket can include a heating element assembly. The blanket can further include a power source coupled to the heating element assembly. The power source can be adapted to supply power to the heating element assembly. The blanket can further include a controller adapted to control the supply of power from the power source. The blanket can further include a temperature sensor assembly adapted to monitor the temperature of the heating element assembly and provide the heating element assembly temperature to the controller. The controller can be adapted to compare the heating element assembly temperature to a threshold temperature. The blanket can further include a timer operatively coupled to the controller. The controller can be adapted to determine from the timer whether a time limit has elapsed. The time limit can be less than a thermal burn injury time. The controller can be further adapted to reduce the supply of power to the heating element assembly when the time limit has elapsed before the heating element assembly temperature meets or exceeds the threshold temperature.

In a second aspect, the present invention provides an electric warming blanket. The blanket can include a heating element assembly and a power source similar to those of the first aspect. The blanket can further include a controller adapted to control the supply of power from the power source. The blanket can further include a temperature sensor assembly adapted to measure a temperature of the heating element assembly and provide the temperature to the controller. The power source can be adapted to supply power to the heating element assembly until the controller determines from the temperature sensor assembly that a threshold temperature is reached. The blanket can further include a timer operatively coupled to the controller. The controller can be adapted to determine from the timer whether a time limit has elapsed. The controller can be further adapted to (a) shut off the supply of power to the heating element assembly when the time limit has elapsed and (b) reset the timer when the heating element assembly temperature meets or exceeds the threshold temperature.

In a third aspect, the present invention provides an electric warming blanket for warming patients during surgery and other medical procedures. The blanket can include a heating element assembly and a power source similar to those of the first aspect. The blanket can further include a controller adapted to control the supply of power from the power source. The blanket can further include means for monitoring the temperature of the heating element assembly. The controller can be adapted to compare the heating element assembly temperature to a threshold temperature. The blanket can further include a timer operatively coupled to the controller. The controller can be adapted to determine from the timer whether a time limit has elapsed. The time limit can be less than a thermal burn injury time. The controller can be further adapted to (a) reduce the supply of power to the heating element assembly when the time limit has elapsed and (b) reset the timer when the heating element assembly temperature meets or exceeds the threshold temperature.

In a fourth aspect, the present invention provides a method of controlling the temperature of an electric warming blanket, perhaps like those discussed in the first, second, or third aspects. The method can include supplying power to a heating element assembly. The method can further include measuring a temperature of the heating element assembly. The method can further include determining whether the measured temperature reaches a threshold. The method can further include interrupting the supply of power after the measured temperature reaches the threshold. The method can further include timing the period of time of the supply of power. The method can further include interrupting the supply of power when the period of time reaches a time limit. Some embodiments further include resuming the supply of power to the heating element assembly after the measured temperature drops below the threshold, and restarting the timing upon the resumption of the supply of power.

Embodiments of the present invention can include one or more of the following features. In some embodiments, the controller is adapted to reset the timer after the heating element assembly temperature meets or exceeds the threshold temperature. In some embodiments, the timer is started when the controller starts the supply of power. In some embodiments, the start of the supply of power occurs after the heating element assembly temperature falls below the threshold temperature. In some embodiments, the controller is adapted to shut off the supply of power to the heating element assembly when the time limit has elapsed. In some embodiments, the controller is adapted to prompt the power source to supply power to the heating element assembly when the heating element assembly temperature is below the threshold temperature. In some embodiments, the controller is adapted to reduce the supply of power to the heating element assembly after the heating element assembly temperature meets or exceeds the threshold temperature. In some embodiments, the controller is adapted to increase the supply of power to the heating element assembly as the heating element assembly temperature drops below the threshold temperature. In some embodiments, the power source is adapted to supply power to the heating element assembly until the heating element assembly temperature equals the threshold temperature. In some embodiments, the threshold temperature is between 37 and 43° C. In some embodiments, the heating element assembly has a generally uniform watt density output of less than approximately 0.5 watts/square inch. In some embodiments, the controller is adapted to trigger one or more alarms when the time limit has elapsed. In some such embodiments, the one or more alarms includes at least one of a visible alarm and an audible alarm.

In some embodiments, the time limit is less than about 20 minutes. In some such embodiments, the time limit is between about 5 and about 15 minutes. In some such embodiments, the time limit is about 10 minutes.

In some embodiments, the controller is adapted to reduce the supply of power to the heating element assembly as the heating element assembly temperature increases toward the threshold temperature. In some such embodiments, the controller is further adapted to reset the timer when the supply of power falls below a threshold level. In some such embodiments, the controller is a PID controller adapted to monitor an integral control term, the controller being further adapted to reset the timer when the integral control term reaches a threshold level.

In some embodiments, the controller is adapted to set the time limit based on whether the heating element assembly has reached a steady state operation for a period of time. In some embodiments, the time limit is reduced once the heating element assembly has first reached a steady state operation.

In some embodiments, the means for monitoring the temperature of the heating element assembly includes a plurality of temperature sensors coupled to the controller. In some such embodiments, the temperature sensors are adapted to measure temperatures of different portions of the heating element assembly. In some such embodiments, the power source is adapted to supply power to the heating element assembly until the controller determines that the threshold temperature from one of the temperature sensors is reached. In some such embodiments, the power source is adapted to supply power to the heating element assembly until the controller determines that the average temperature reaches the threshold temperature.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads.

Figure 1:
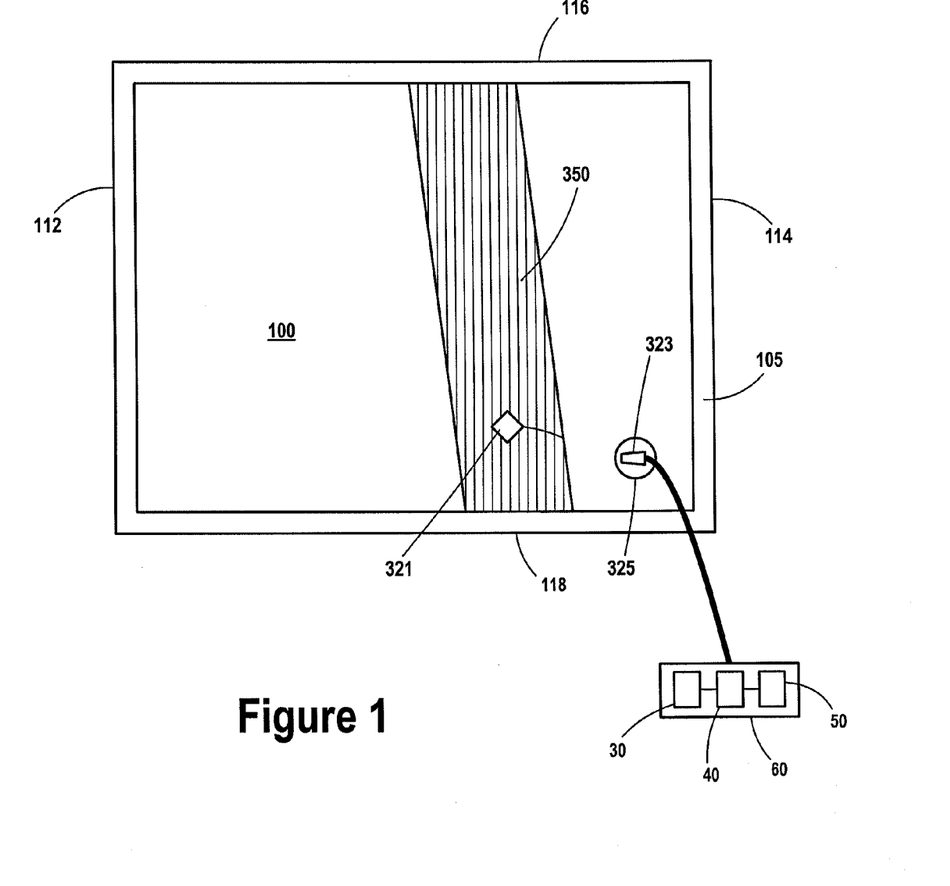
FIG. 1 is a top plan view of a heating blanket, according to some embodiments of the present invention.

FIG. 1 shows a heating blanket 100 according to some embodiments of the present invention. As shown, the heating blanket 100 is generally rectangular. Embodiments of the present invention can be used in connection with a wide variety of heating blankets. For example, in some cases, the heating blanket can be a blanket sized and shaped for the upper body or upper body limb (e.g., a wrap-around blanket), or a blanket sized and shaped for the lower body or lower body limb. In some cases the heating blanket can be used in conjunction with a disposable cover.

The heating blanket 100 of FIG. 1 includes a shell 105 that can be durable and waterproof. As shown, a portion of the shell 105 is cut away, revealing a heating element assembly 350. The heating element assembly 350 is generally covered by the shell and can extend within the shell 105 between edge 112 and edge 114 and between edge 116 and edge 118. An electrical connector housing 325 and a corresponding connector plug 323 can be coupled to the shell 105, thereby enabling access to a temperature sensor assembly such as those discussed below.

The shell 105 can protect and isolate the heating element assembly 350 from an external environment of heating blanket 100. The shell 105 can include a water-resistant material layer that can form a substantially hermetic seal around the heating element assembly 350. The shell 105 can provide further protection to a patient disposed beneath heating blanket 100 against electrical shock hazards. According to preferred embodiments of the present invention, shell 105 is waterproof to prevent fluids (e.g., bodily fluids, IV fluids, cleaning fluids, etc.) from contacting the heating element assembly 350. In some preferred embodiments, shell 105 may further include an anti-microbial element (e.g., a SIL-VERion™ antimicrobial fabric available from Domestic Fabrics Corporation or Ultra-Fresh™ from Thomson Research Associates).

According to an illustrative embodiment of the present invention, shell 105 comprises a nylon fabric having an overlay of polyurethane coating to provide waterproofing. The coating can be on at least an inner surface of each of the two sheets, further facilitating a heat seal between the two sheets, according to preferred embodiments. It should be noted that, according to some embodiments of the present invention, a covering for heating element assemblies may be removable and, thus, include a reversible closure facilitating removal of a heating element assembly 350 therefrom and insertion of the same or another heating element assembly 350 therein. In some embodiments, shell 105 comprises a PVC film of sufficient thickness to provide the necessary strength. In some such embodiments, the edge seals can be softer.

In some embodiments, one or more layers may be positioned between the heating element assembly 350 and the shell 105. For example, in some embodiments, a layer of thermally insulating material (e.g., polymeric foam or high-loft fibrous non-woven material) can be included in one or more locations. In some instances, a layer of thermally insulating material can be positioned to protect a portion of the patient from the heating element assembly 350 in the event that part of the shell 105 is inadvertently placed under that portion of the patient. In such instances, a layer of thermal insulating material can be positioned between the heating element assembly 350 and the patient-contacting surface of the shell 105. In this way, in the event that part of the shell 105 is inadvertently placed under that portion of the patient, that portion of the patient can contact an insulated portion of the shell 105 rather than a non-insulated portion of the shell 105.

In some instances a layer of thermally insulating material can be positioned to make sure that a maximal amount of heat being generated by the heating element assembly 350 is transferred to the patient. In such instances, a layer of thermally insulating material can help insulate the heating element assembly 350 from the environment and provide a more uniform temperature distribution. The layer of thermally insulating material can be positioned between the heating element assembly 350 and the surface of the shell 105 that does not contact the patient. In this way, a maximal amount of heat being generated by the heating element assembly 350 can be transferred to the patient and not to the surrounding environment.

In some instances a layer of thermally insulating material can be positioned to prevent caregivers from experiencing unwanted contact with activated heating blankets. Other layers (e.g., an electrically insulating layer similar to those discussed elsewhere herein) can be positioned between the heating element assembly 350 and the shell 105.

Figure 2A:
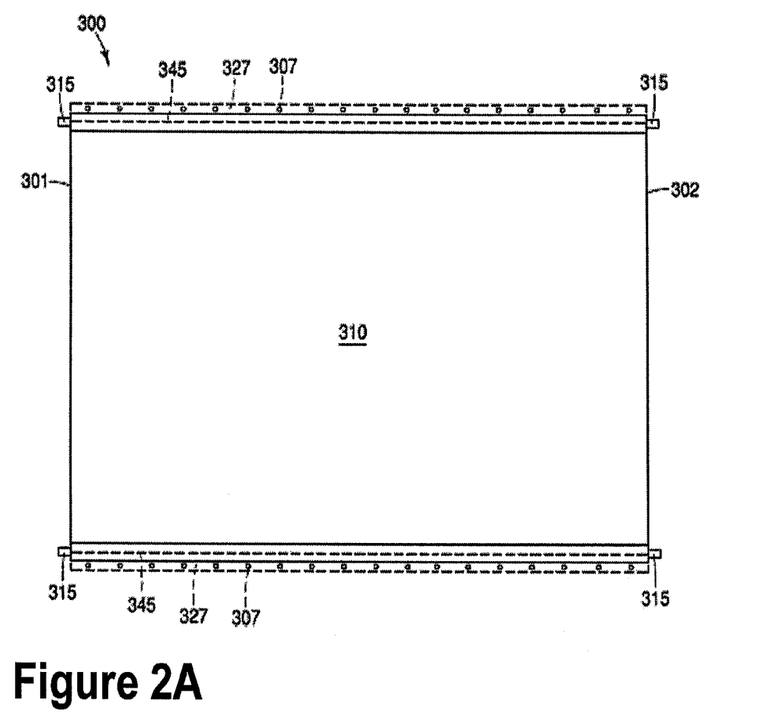
FIG. 2A is a plan view of a flexible heating blanket subassembly for a heating blanket, according to some embodiments of the present invention.
Figure 2B:
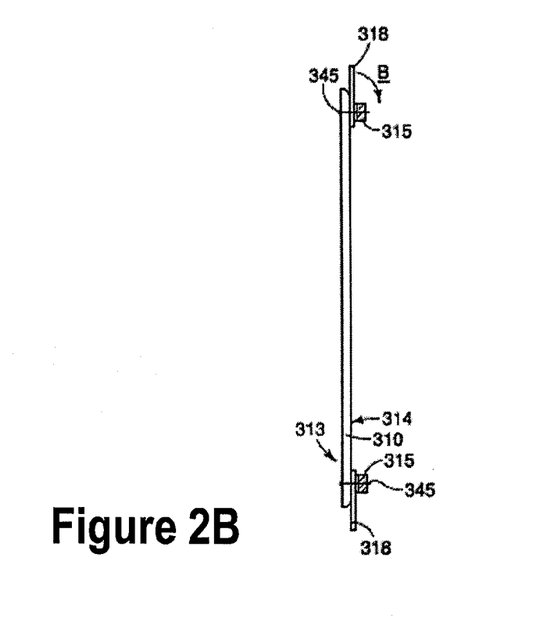
FIG. 2B is an end view of some embodiments of the subassembly shown in FIG. 2A.

FIGS. 2A-2B show an illustrative heating blanket subassembly 300 that can be incorporated into heating element assemblies (e.g., heating element assembly 350 of FIG. 1) in some embodiments of the present invention. Referring again to FIGS. 2A-2B, in many embodiments, the heating blanket subassembly 300 is flexible. The heating blanket subassembly 300 can include a flexible sheet-like heating element 310, or heater, which can include a first side edge 301 and a second side edge 302. According to preferred embodiments of the present invention, heating element 310 comprises a conductive fabric or a fabric incorporating closely spaced conductive elements such that heating element 310 has a substantially uniform watt density output, preferably less than approximately 0.5 watts/sq. inch, and more preferably between approximately 0.2 and approximately 0.4 watts/sq. inch, across a surface area, of one or both sides 313, 314 (FIG. 2B).

Some examples of conductive fabrics which may be employed by embodiments of the present invention include, without limitation, carbon fiber fabrics, fabrics made from carbonized fibers, conductive films, or woven or non-woven non-conductive fabric or film substrates coated with a conductive material, for example, polypyrrole, carbonized ink, or metalized ink. In many embodiments, the conductive fabric is a polymeric fabric coated with a conductive polymeric material such as polypyrrole. In addition, the flexible heating element 310 may be made from a matrix of electrically resistant wire or metal traces attached to a fibrous or film material layer.

FIG. 2A further illustrates subassembly 300 including two bus bars 315 coupled to heating element 310 for powering heating element 310. Each bar 315 is shown extending between first and second side edges 301, 302. With reference to FIG. 2B, according to some embodiments, bus bars 315 are coupled to heating element 310 by a stitched coupling 345 (e.g., formed with conductive thread such as silver-coated polyester or nylon thread (Marktek Inc., Chesterfield, Mo.)).

As shown, insulation is provided between the bus bars 315 and the heating element 310. FIG. 2B illustrates subassembly 300 wherein insulating members 318 (e.g., fiberglass material strips having an optional PTFE coating and a thickness of approximately 0.003 inch) extend between bus bars 315 and heating element 310 at each stitched coupling 345, so that electrical contact points between bars 315 and heating element 310 are solely defined by the conductive thread of stitched couplings 345. Alternatively, the electrical insulation material layer could be made of polymeric film, a polymeric film reinforced with a fibrous material, a cellulose material, a glass fibrous material, rubber sheeting, polymeric or rubber coated fabric or woven materials or any other suitable electrically insulating material.

Each of the conductive thread stitches of coupling 345 can maintain a stable and constant contact with bus bar 315 on one side and heating element 310 on the other side of insulating member 318. The stitches produce a stable contact in the face of any degree of flexion, so that the potential problem of intermittent contact between bus bar 315 and heating element 310 (that could arise for the embodiment shown in FIG. 2B, where bus bar 315 is in physical contact with heating element 310) can be avoided. The stitches are the only electrical connection between bus bar 315 and heating element 310, but, since the conductive thread has a much lower electrical resistance than the conductive fabric of heating element 310, the thread does not heat under normal conditions.

In addition to heating blanket applications described herein, such a design for providing for a uniform and stable conductive interface between a bus bar and a conductive fabric heating element material can be used in other applications. For example, such a design can improve the conductive interface between a bus bar or electrode and a conductive fabric in non-flexible heating elements, in electronic shielding, in radar shielding and other applications of conductive fabrics.

In some preferred embodiments, coupling 345 includes two or more rows of stitches for added security and stability. However, due to the flexible nature of blanket subassembly 300, the thread of stitched couplings 345 may undergo significant stresses. These stresses, over time and with multiple uses of a blanket containing subassembly 300, could lead to one or more fractures along the length of stitched coupling 345. Such a fracture, in other designs, could also result in intermittent contact points, between bus bar 315 and heating element 310, that could lead to a thermal breakdown of heating element 310 along bus bar. But, if such a fracture were to occur in the embodiment of FIG. 2B, insulating member 318 may prevent a thermal breakdown of heating element 310, so that only the conductive thread of stitched coupling 345 melts down along bus bar 315. According to some preferred embodiments, more than two rows of stitches are applied to each bus bar 315 for added safety and stability of the bus bar/heating element interface.

Alternative threads or yarns employed by embodiments of the present invention may be made of other polymeric or natural fibers coated with other electrically conductive materials. In addition, nickel, gold, platinum and various conductive polymers can be used to make conductive threads. Metal threads such as stainless steel, copper or nickel could also be used for this application.

According to an exemplary embodiment, bars 315 are comprised of flattened tubes of braided wires, such as are known to those skilled in the art (e.g., a flat braided silver coated copper wire) and may thus accommodate the thread extending therethrough, passing through openings between the braided wires thereof. In addition such bars are flexible to enhance the flexibility of blanket subassembly 300. According to alternate embodiments, bus bars 315 can be a conductive foil or wire, flattened braided wires not formed in tubes, an embroidery of conductive thread, or a printing of conductive ink. Preferably, bus bars 315 are each a flat braided silver-coated copper wire material, since a silver coating has shown superior durability with repeated flexion, as compared to tin-coated wire, for example, and may be less susceptible to oxidative interaction with a polypyrrole coating of heating element 310 according to an embodiment described below. Additionally, an oxidative potential, related to dissimilar metals in contact with one another is reduced if a silver-coated thread is used for stitched coupling 345 of a silver-coated bus bar 315.

According to an exemplary embodiment, a conductive fabric comprising heating element 310 comprises a non-woven polyester having a basis weight of approximately 170 g/m$^2$ and being 100% coated with polypyrrole (available from Eeonyx Inc., Pinole, Calif.). The coated fabric has an average resistance (e.g., determined with a four point probe measurement) of approximately 15 ohms per square inch. This average resistance is suitable to produce the preferred watt density of 0.2 to 0.4 watts/sq. in. for surface areas of heating element 310 having a width, between bus bars 315, in the neighborhood of about 19 to 28 inches, when powered at about 48 volts. In some embodiments, the basis weight of the non-woven polyester may be chosen in the range of approximately 80-180 g/m$^2$. However, other basis weights may be engineered to operate adequately are therefore within the scope of embodiments of the invention.

A resistance of such a conductive fabric may be tailored for different widths between bus bars (wider requiring a lower resistance and narrower requiring a higher resistance) by increasing or decreasing a surface area of the fabric that can receive the conductive coating. In some instances, this can be achieved by increasing or decreasing the basis weight of the nonwoven. Resistance over the surface area of the conductive fabrics is generally uniform in many embodiments of the present invention. However, the resistance over different portions of the surface area of conductive fabrics such as these may vary (e.g., due to (a) variation in a thickness of a conductive coating, (b) variation within the conductive coating itself, (c) variation in effective surface area of the substrate which is available to receive the conductive coating, or (d) variation in the density of the substrate itself). Local surface resistance across a heating element, for example heating element 310, is directly related to heat generation according to the following relationship:

$$Q(\text{Joules}) = I^2(\text{Amps}) \times R(\text{Ohms})$$

Variability in resistance thus translates into variability in heat generation, which can ultimately manifest as a variation in temperature.

According to preferred embodiments of the present invention, which are employed to warm patients undergoing surgery, precise temperature control is desirable. Means for determining heating element temperatures, which average out temperature variability caused by resistance variability across a surface of the heating element, are described below in conjunction with FIG. 3A.

Referring again to FIGS. 2A-2B, the flexibility of blanket subassembly 300 can allow blanket subassembly 300 to conform to the contours of a body (e.g., all or a portion of a patient undergoing surgery). This flexibility can be provided primarily by flexible heating element 310 and can be optionally enhanced by the incorporation of flexible bus bars. Conforming to the contours of a patient's body is preferable to simply bridging across high spots of the body. Such conformance may optimize a conductive heat transfer from heating element 310 to a surface of the body.

The uniform watt-density output across the surface areas of preferred embodiments of heating element 310 translates into generally uniform heating of the surface areas, but not necessarily a uniform temperature. For example, at locations of heating element 310 which are in conductive contact with a body acting as a heat sink, the heat is efficiently drawn away from heating element 310 and into the body (e.g., by blood flow). At the same time, at those locations where heating element 310 does not come into conductive contact with the body, an insulating air gap exists between the body and those portions, so that the heat is not drawn off those portions as easily. Therefore, those portions of heating element 310 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 310. Since the heat generation is generally uniform, the heat flux to the patient will also be generally uniform. However, at the non-contacting locations, the temperature is higher to achieve the same flux as the contacting portions. Some of the extra heat from the higher temperatures at the non-contacting portions can therefore be dissipated out the back of the pad instead of into the patient.

Although radiant and convective heat transfer are more efficient at higher heater temperatures, the laws of thermodynamics dictate that as long as there is a uniform watt-density of heat production, even at the higher temperature, the radiant and convective heat transfer from a blanket of this construction will result in a generally uniform heat flux from the blanket. Therefore, by controlling the 'contacting' portions to a safe temperature (e.g., via a temperature sensor assembly 321 coupled to heating element 310 in a location where heating element 310 will be in conductive contact with the body), the 'non-contacting' portions, will also be operating at a safe temperature because of the less efficient radiant and convective heat transfer.

According to preferred embodiments, heating element 310 comprises a conductive fabric having a relatively small thermal mass. When a portion of such a heating element that is operating at the higher temperature is touched, suddenly converting a 'non-contacting' portion into a 'contacting' portion, that portion will cool almost instantly to the lower operating temperature.

Figure 3A:
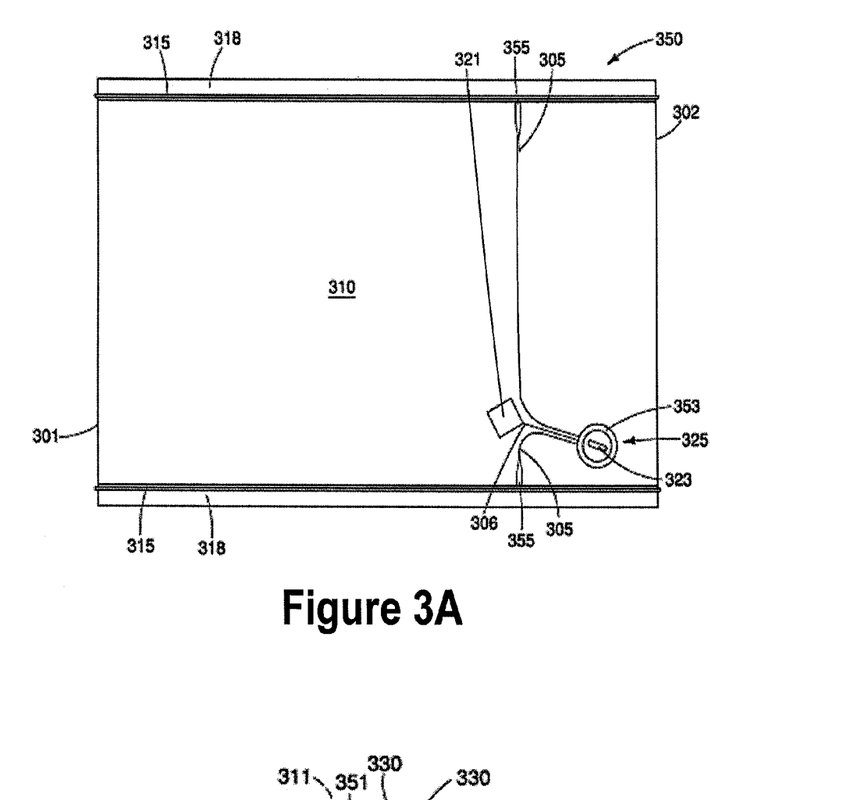
FIG. 3A is a top plan view of a heating element assembly, according to some embodiments of the present invention, which may be incorporated in the blanket shown in FIG. 1.
Figure 3B:
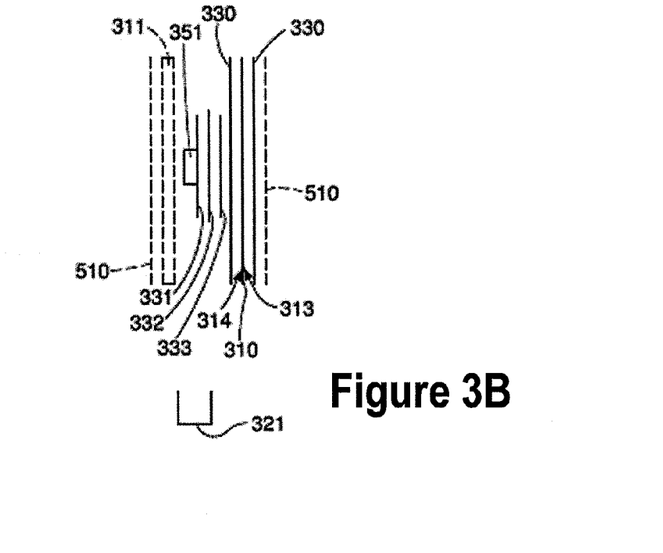
FIG. 3B is a section view of the temperature sensor assembly of FIG. 3A.

FIGS. 3A-3B show a heating element assembly 350 similar to the heating element assembly 350 of FIG. 1. Referring again to FIGS. 3A-3B, the heating element assembly can include a temperature sensor assembly 321. As shown, the temperature sensor assembly 321 is coupled to heating element 310 at a location where heating element 310 would come into conductive contact with the patient. This can assist in maintaining a safe temperature distribution across heating element 310. The more constant the temperature information, the more the temperature controller can rely on it in controlling the heater temperature. In some embodiments, the temperature sensor assembly 321 can even be provided separately from the heating blanket.

According to embodiments of the present invention, zones of heating element 310 may be differentiated according to whether or not portions of heating element 310 are in conductive contact with a body (e.g., a patient undergoing surgery). In some embodiments, the threshold temperature is between 37 and 43° C. In one particular embodiment, the threshold temperature is 43° C. A temperature of 43° C. has been shown to provide beneficial warming to a patient without providing excessive heat. In the case of conductive heating, gentle external pressure may be applied to a heating blanket including heating element 310. Such pressure conforms heating element 310 into better conductive contact with the patient to improve heat transfer. However, if excessive pressure is applied, the blood flow to that skin may be reduced at the same time that the heat transfer is improved and this combination of heat and pressure to the skin can be dangerous. It is well known that patients with poor perfusion should not have prolonged contact with temperatures in excess of approximately 42° C. Several studies show 42° C. to be the highest skin temperature that cannot cause thermal damage to normally perfused skin, even with prolonged exposure. (Stoll & Greene, Relationship Between Pain and Tissue Damage Due to Thermal Radiation. J. Applied Physiology 14(3):373-382.1959; and Moritz and Henriques, Studies of Thermal Injury: The Relative Importance of Time and Surface Temperature in the Causation of Cutaneous Burns. Am. J. Pathology 23:695-720, 1947). Thus, according to certain embodiments of the present invention, the portion of heating element 310 that is in conductive contact with the patient is controlled to approximately 43° C. in order to achieve a temperature of about 41-42° C. on a surface of a heating blanket cover that surrounds heating element 310 (e.g., shell 105 of FIG. 1).

FIG. 3B illustrates the temperature sensor assembly 321 assembled on side 314 of the heating element 310. As shown, the heating element 310 is overlaid on both sides 313, 314 with an electrically insulating layer 330. The electrically insulating layer 330 is preferably formed of a flexible non-woven very low loft fibrous material (e.g., 1.5 ounces-per-square-yard nylon), which is preferably laminated to sides 313, 314 with a hotmelt laminating adhesive. In some embodiments, the adhesive is applied over the entire interfaces between insulating layer 330 and heating element 310. Other examples of suitable materials for insulating layer 330 include, without limitation, polymeric foam, a woven fabric, such as cotton or fiberglass, and a relatively thin plastic film, cotton, and a non-flammable material, such as fiberglass or treated cotton. According to preferred embodiments, overlaid insulating layers 330 prevent electrical shorting of one portion of heating element 310 with another portion of heating element 310 if heating element 310 is folded over onto itself Many such embodiments prevent electrical shorting without compromising the flexibility of heating assembly 350. Heating element assembly 350 may be powered by a relatively low voltage (approximately 48V). Insulating layers 330 may even be porous in nature to further maintain the desired flexibility of assembly 350.

As shown in FIG. 3A, an assembly of leads 305, 306 and junctions 355 can connect the bus bars 315 and the temperature sensor assembly 321 to an electrical connector housing 325. Leads 305 couple the connector housing 325 to bus bars 315 at junctions 355. Lead 306 couples the temperature sensor assembly 321 to the connector housing 325. In many embodiments, leads 305, 306 extend over any insulating layer (e.g., 330 in FIG. 3B) and into the electrical connector housing 325. As is noted above (see discussion in connection with FIG. 1) and discussed in greater detail below (see discussion in connection with FIG. 4A), electrical connector housing 325 can contain a connector plug 323.

Returning now to FIG. 3B, the illustrative temperature sensor assembly 321 will be described in greater detail. The temperature sensor assembly 321 can include a temperature sensor 351 (e.g., a surface mount chip thermistor (such as a Panasonic ERT-J1VG103FA: 10K, 1% chip thermistor)) soldered to an etched metal foil. In many embodiments, a substrate 331 (e.g., of polyimide (Kapton)) surrounds the temperature sensor 351. A heat spreader 332 (e.g., a copper or aluminum foil) can be mounted to an opposite side of substrate 331 (e.g., being bonded with a pressure sensitive adhesive). Substrate 331 can be relatively thin (e.g., about 0.0005-inch thick) so that heat transfer between heat spreader 332 and sensor is not significantly impeded.

In some embodiments, the temperature sensor 351 is positioned such that the regions surrounding sensor 351 will be in conductive contact with the body when a heating blanket is placed over a body. As previously described, in many instances, it is desirable that a temperature of approximately 43° C. be maintained over a surface of heating element 310 which is in conductive contact with a body of a patient undergoing surgery. An additional alternate embodiment is contemplated in which an array of temperature sensors are positioned over the surface of heating element 310, being spaced apart to collect temperature readings. In some such embodiments, the collected temperatures can be averaged to account for resistance variance.

Figure 4A:
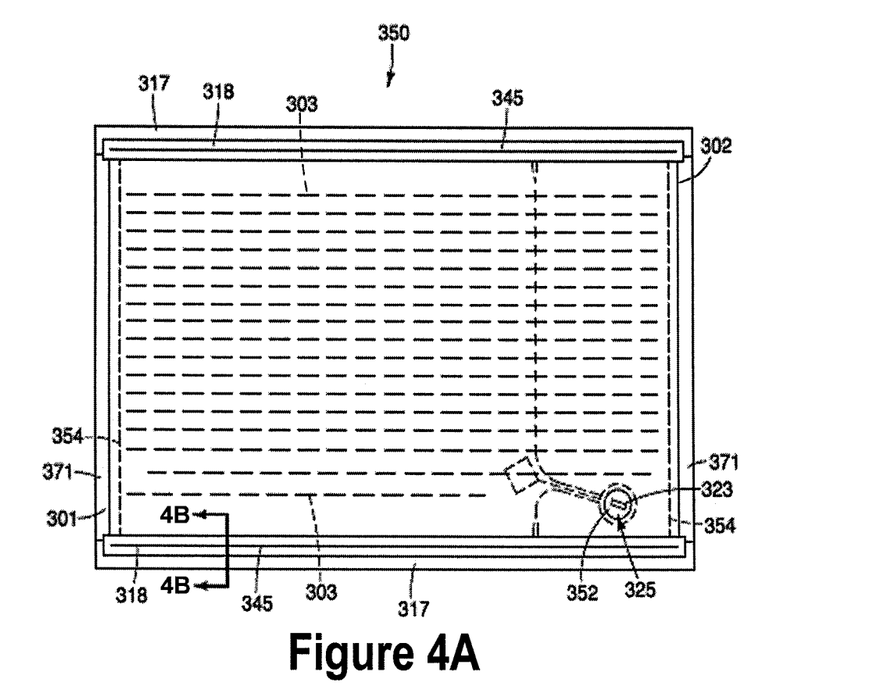
FIG. 4A is a top plan view of a heating element assembly, which may be incorporated in the blanket shown in FIG. 1.
Figure 4B:
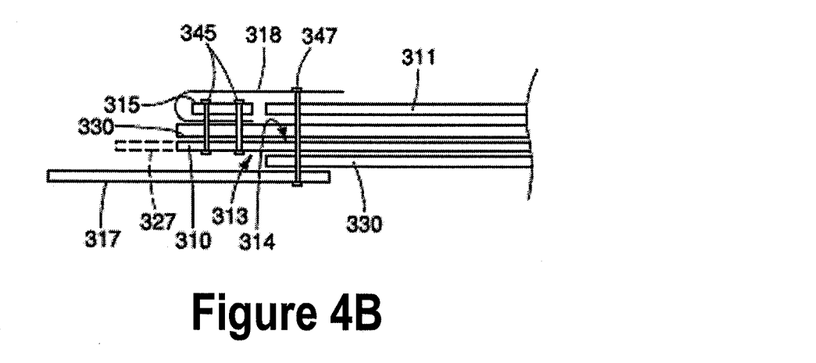
FIG. 4B is a cross-section view through section line 4B-4B of FIG. 4A.

FIGS. 4A-4B show a heating element assembly 350 that may be incorporated into a heating blanket (e.g., heating blanket 100 of FIG. 1). As shown, the heating element assembly 350 includes heating element 310 overlaid with electrical insulation 330 on both sides 313, 314 and thermal insulation layer 311 extending over the top side 314 thereof (dashed lines show leads and sensor assembly beneath layer 311).

A heating blanket may include a layer of thermal insulation 311 extending over a top side (corresponding to side 314 of heating element 310 as shown in FIG. 2B) of heating assembly 350 as discussed above. According to the illustrated embodiment, layer 311 is inserted beneath a portion of each insulating member 318. The insulating members 318 have been folded over the respective bus bar 315 (e.g., as illustrated by arrow B in FIG. 2B), and then held in place by a respective row of non-conductive stitching 347 that extends through insulating member 318, layer 311 and heating element 310. Although not shown, it should be appreciated that layer 311 may further extend over bus bars 315. Although insulating layer 330 is shown extending beneath layer 311 on side 314 of heating element 310, according to alternate embodiments, layer 311 independently performs as a thermal and electrical insulation so that insulating layer 330 is not required on side 314 of heating element 310. FIG. 4A further illustrates, with longitudinally extending dashed lines, a plurality of optional slits 303 in layer 311, which may extend partially or completely through layer 311, in order to increase the flexibility of assembly 350. Such slits are desirable if a thickness or density of layer 311 is such that it prevents the heating blanket from draping effectively about a patient. The optional slits are preferably formed, for example, extending only partially through layer 311 starting from an upper surface thereof, to allow bending of the heating blanket about a patient and to prevent bending of the heating blanket in the opposition direction.

Returning now to FIG. 3A, to be referenced in conjunction with FIGS. 1 and 4A, connector housing 325 and connector plug 323 will be described in greater detail. According to certain embodiments, housing 325 is an injection molded thermoplastic (e.g., PVC) and may be coupled to assembly 350 by being stitched into place, over insulating layer 330. FIG. 3A shows housing 325 including a flange 353 through which such stitching can extend.

Referring to FIGS. 1 and 4A, in some embodiments, a surface of flange 353 of housing 325 protrudes through a hole formed in thermal insulating layer 311 so that a seal may be formed (e.g., by adhesive bonding and/or heat sealing) between an inner surface of shell 105 and surface 352. According to one embodiment, wherein housing 325 is injection molded PVC and the inner surface of shell 105 is likewise PVC, housing 325 is sealed to shell 105 via a solvent bond. It may be appreciated that the location of the connector plug 323 is suitable to keep the corresponding connector cord well away from the surgical field. In embodiments in which the inner surface of shell 105 is coated with polyurethane and the housing 325 is injection molded PVC, an intermediate adhesive can be used to allow for a heat seal connection (e.g., a solvent bond adhesive can be applied to the housing 325, and the polyurethane film can be heat sealed to the exposed adhesive).

FIGS. 4A-4B further illustrate a pair of securing strips 317, each extending laterally from and alongside respective lateral portions of heating element 310, parallel to bus bars 315, and each coupled to side 313 of heating element 310 by the respective row of non-conductive stitching 347. Another pair of securing strips 371 is shown in FIG. 4A, each strip 371 extending longitudinally from and alongside respective side edges 301, 302 of heating element 310 and being coupled thereto by a respective row of non-conductive stitching 354. Strips 371 may extend over layer 311 or beneath heating element 310. As shown, strips 317 preferably extend over conductive stitching of stitched coupling 345 on side 313 of heating element 310. The strips 317 can provide a layer of insulation that can prevent shorting between portions of side 313 of heating element 310 if heating element 310 were to fold over on itself along rows of conductive stitching of stitched coupling 345 that couple bus bars 315 to heating element 310. In some embodiments, strips 317 may alternately extend over insulating member 318 on the opposite side of heating element 310. According to the illustrated embodiment, securing strips 317 and 371 are made of a polymer material (e.g., PVC). They may be heat sealed between the sheets of shell (105 of FIG. 1) in corresponding areas of the heat seal zone in order to secure heating element assembly 350 within a corresponding gap between the two sheets of shell (105 of FIG. 1). According to an alternate embodiment, for example, shown by dashed lines in FIGS. 2A and 4B, heating element 310 extends laterally out from each bus bar 315 to a securing edge 327, which may include one or more slots or holes 307 extending therethrough so that inner surfaces of sheets of shell (105 of FIG. 1) can contact one another to be sealed together and thereby hold edges 327.

Referring to FIG. 1, connector plug 323 can protrude from shell 105 of the heating blanket 100. An extension cable may couple the heating element assembly 350 to a console 60. The console 60 includes a shut-off timer 30 and a power source 50 each coupled to a control system (or controller) 40. The shut-off timer 30 can be operatively coupled to the control system 40, meaning that the shut-off timer 30 can be integrated into the control system 40, the shut-off timer 30 can be a separate component, or the shut-off timer 30 and the control system 40 can have any other suitable functional relationship. The temperature sensor assembly 321 can be configured to provide temperature information to the control system 40, which may act as a temperature controller. The controller may function to interrupt such power supply (e.g., in an over-temperature condition) or to modify the duty cycle to control the heating element temperature.

The power source 50 and power type can be any type known in the art. In certain embodiments, the power source 50 supplies a straight-line DC voltage to the control system 40, and the control system 40 provides a pulse-width-modulated voltage (e.g., at a 75% duty cycle) to the heating element assembly 350. Of course, other duty cycles and/or voltage levels can be used based on the design of the blanket and its heating element in order to achieve a desired threshold temperature in a reasonable amount of time. Too high of voltage or duty cycle, while decreasing the time to reach the desired temperature threshold, may increase the amount of temperature overshoot before the control system reduces or shuts off power. Moreover, in the case of temperature sensor failure, thermal runaway presents a greater concern with relatively higher voltage or duty cycle settings. Too low of a voltage or duty cycle may cause unreasonably long warm-up times.

The operation of the heating blanket 100 will now be described. In operation, the control system 40 is first turned on and prompts the power source 50 to begin supplying power to the heating element assembly 350. The heating element assembly 350 continues to receive this power until the temperature sensor assembly 321 senses a threshold temperature. Any type of duty cycle and voltage level can be used, so long as a desired threshold temperature is achieved in a reasonable amount of time. The threshold temperature can be any desired temperature that medical personnel wish to supply to a patient. In some embodiments, the threshold temperature is 32° C., 35° C., 43° C., or other temperatures as discussed elsewhere herein. Some patients (e.g., those with poor blood perfusion) should not have prolonged contact with conductive heat in excess of approximately 42° C., as is discussed elsewhere herein. Thus, according to certain embodiments, the threshold temperature sensor is set to approximately 43° C. in order to achieve a temperature of about 41-42° C. on a surface of the heating blanket. The skin temperature may or may not reach this threshold temperature of the heating blanket 100. In many cases, the skin temperature is slightly below the threshold temperature.

Once the temperature sensor assembly 321 senses the threshold temperature, control system 40 prompts the power source 50 to stop supplying power to the heating element assembly 350. At some point after the power supply is stopped, the temperature of the heating blanket 100 cools to below the threshold temperature. Once the temperature sensor assembly 321 senses a temperature below the threshold temperature, the control system 40 prompts the power source 50 to again supply power to the heating element assembly 350. This process operates much like common thermostats and continues until the control system 40 is shut off by the medical personnel.

The shut-off timer 30 operates simultaneously during the process just described. Regardless of the temperature sensed by the temperature sensor assembly 321, the shut-off timer 30 limits the amount of time that power is supplied to heating element assembly 350. This way, in case the temperature sensor assembly 321 never reaches the threshold temperature (even though other areas of the blanket are at or above the threshold temperature), the shut-off timer 30 only allows the power to be supplied for a limited time. This is an additional safety feature that helps to prevent patients from being exposed to temperatures at or above the threshold temperatures for a prolonged period of time.

The operation of the shut-off timer 30 will now be described in accordance with one embodiment. Once the control system 40 is turned on, it prompts the shut-off timer 30 to start. The shut-off timer 30 runs for a desired period of time and upon expiration of this period of time, the control system 40 prompts the power source 50 to stop supplying power to the heating element assembly 350. In addition, the control system 40 may sound an audio alarm and/or display a visible cue to let medical personnel know that the desired time period has expired. The expiration of the time period tells the medical personnel that the temperature sensor assembly 321 may not be working.

If the temperature sensor assembly 321 is functioning properly, the shut-off timer 30 should not run until the end of the desired time period. Each time the temperature sensor assembly 321 reaches the threshold temperature, the control system 40 prompts the power source 50 to stop supplying power and also stops and resets the shut-off timer 30. Once the sensed temperature cools, the control system 40 prompts the power source 50 to again supply power and also starts the shut-off timer 30. This process continues throughout normal operation of the heating blanket 100. Should the temperature sensor assembly 321 ever malfunction and fail to sense a threshold temperature within the timer time period, the control system 40 will prompt the power source 50 to stop supplying power and will trigger an alarm. The medical personnel would either "repair" the heating blanket 100 (e.g., by removing a metal pan or other object that may be tricking the sensor or replace the blanket with a new one). Thus, the heating blanket 100 has an additional safety feature to protect patients.

The period of time selected for the shut-off timer 30 is a time period that is less than a time it takes for thermal burn injury to occur with a particular blanket ("thermal burn injury time"). The thermal burn injury time may vary depending on the type of blanket, the watt density of the blanket and/or the type of power supplied to such blanket.

The thermal burn injury time can also vary depending on whether the temperature sensor assembly 321 stops providing accurate readings (e.g., malfunctions, heat sink placed on it, etc.) before the heating blanket 100 begins operation or during operation. For example, if the temperature sensor assembly 321 is not providing reliable data when the heating blanket is first powered up, it is believed that a blanket operating at a watt-density of between about 0.2-0.25 watts/square inch may take 2 to 5 minutes (e.g., 3 minutes) to reach a blanket temperature of 43° C. Of course, the skin temperature will lag behind the blanket temperature in this scenario. It is believed that it may take another 15-20 minutes for the skin temperature to reach 43° C. and yet another 10 minutes for the skin temperature to reach 46° C. Thus the thermal burn injury time in this scenario is at least 27 minutes.

However, under a different scenario, the heating blanket 100 may have already been operating at a steady state for a period of time before temperature sensor assembly 321 suddenly fails (becomes unreliable). In some embodiments, the watt density at steady state operation is between about 0.08-0.12 watts/square inch. Assuming that the blanket temperature was set at its highest setting, 43° C. in one embodiment, the patient skin temperature will be several degrees below the blanket temperature at the time of sensor malfunction. Under this scenario, it is believed that it may take another 10-15 minutes for the skin temperature to reach 43° C. and yet another 10 minutes for the skin temperature to reach 46° C. Thus the thermal burn injury time in this scenario is at least 20 minutes.

In either scenario, it is assumed that the blanket temperature will continue increasing until it hits its own maximum since the power source 50 has not shut off power when reaching the desired blanket temperature setting.

Accordingly, certain embodiments of the invention set the settings of the shut-off timer 30 to numbers lower than those described above, regardless of whether the heating element assembly 350 is just beginning operation or is in the middle of operation and regardless of whether the heating element runs away. In other embodiments of the invention, the control system 40 makes a determination that the blanket has been operating for a period of time at a steady state (e.g., as evidenced by continued cycling of the power supply over a period of time) and adjusts the shut off timer setting lower than its setting for initial start up time.

For blankets operating at a watt density of less than approximately 0.25 watts/square inch, programming the timer 30 for a time period of less than 20 minutes can be desirable. To be extra safe, programming the timer 30 for a time period between about 5 and about 15 minutes can be especially desirable. This time period is well below any thermal burn injury time, in any case, regardless of whether the heating blanket 100 is just beginning operation or is in the middle of operation. Thus, in certain embodiments, the shut-off timer 30 is set to expire after a time period between about 5 and about 15 minutes. In one specific embodiment, the shut-off timer 30 is set to expire after 10 minutes. The time period has a minimum of about 5 minutes in these embodiments because it could take up to 5 minutes for the heating element assembly 350 to even reach the threshold temperature. It would be undesirable to have the time period expire before the threshold temperature is reached under normal operating conditions, as this would be a nuisance to the heating blanket operation.

Of course, blankets operating at a different watt density can have a different time period. The time period can be determined based on the watt density of the blanket. Blankets having a watt density higher than 0.25 watts/square inch might have a time period that is shorter, perhaps less than about 10 minutes. Blankets having a watt density much lower than 0.25 watts/square inch might have a time period that is longer, perhaps more than about 10 minutes. Similarly, blankets operating at a higher watt density (e.g., 0.5 watts/square inch), may have lower time to temperature periods.

The operation of the heating blanket 100 has been described with reference to a temperature sensor assembly 321 having a single temperature sensor, as shown in FIG. 1. Of course, temperature sensor assemblies can be used that have multiple temperature sensors. For example, the temperature sensors can be provided in the form of conventional temperature sensors, over-temperature sensors, and super-over temperature sensors, as described in Applicant's own U.S. application Ser. No. 11/537,189, the contents of which are incorporated herein by reference. In this case, each temperature sensor provides input to the control system 40. The temperature sensors can all have the same threshold temperature or some can have different threshold temperatures. For example, sensors located in an outer area of the blanket that would not be in contact with a patient can have a higher threshold temperature than sensors located in an area that would be in contact with a patient.

The control system 40 can also be configured in any manner so that when a specific temperature scenario is reached, it prompts the power source 50 to stop the supply of power and resets the shut-off timer 30. For example, in one embodiment, the threshold temperature can be the same for each sensor, and the control system 40 takes an average of the overall sensed temperature. When a desired average temperature is reached, the control system 40 shuts off power and resets the shut-off timer 30. Or, the control system 40 can be configured to shut off power and reset the shut-off timer 30 each time a threshold temperature for any sensor is reached. Varieties of scenarios are possible and are within the scope of the invention. In any event, no matter how many sensors are provided and no matter what the threshold temperatures are, the shut-off timer 30 operates the same way. The shut-off timer 30 simply begins when the control system 40 is turned on and continues until either the time period expires or until the control system 40 resets the shut-off timer 30 when a programmed temperature scenario is reached.

Figure 5:
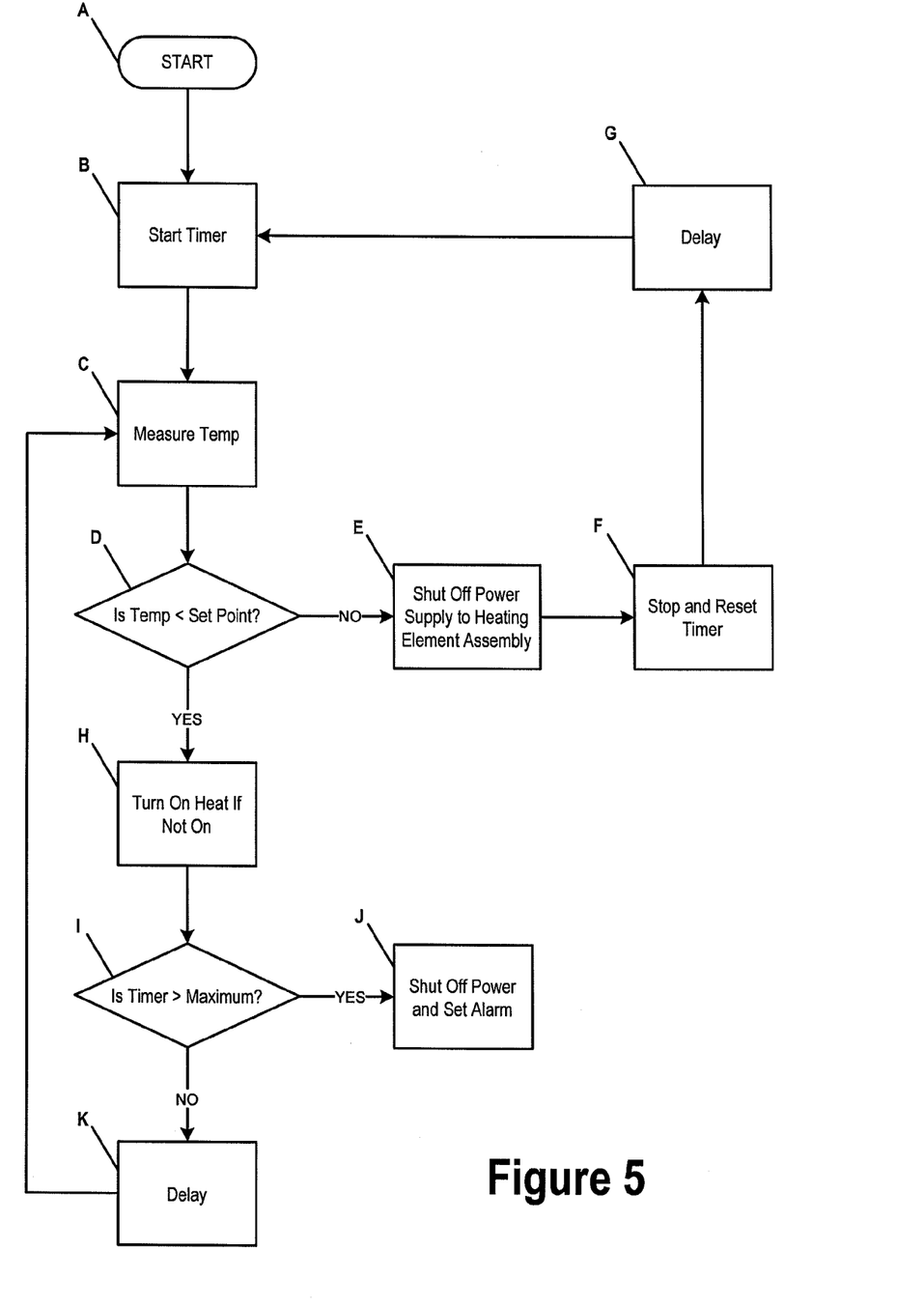
FIG. 5 is a flow diagram showing the operation of a heating blanket, according to some embodiments of the present invention.

FIG. 5 describes one particular embodiment of the operation or programming of the control system 40. At step A, the control system is turned on. This immediately starts the timer at step B and also starts measuring temperatures received from temperature sensors at step C. At step D, the control system determines whether the measured temperature is less than the set point or threshold temperature. If the answer at step D is NO, the control system prompts the power source to shut off the power supply at step E. This in turn stops and resets the timer at step F. The timer delays at step G and then repeats this process starting at step B. If the answer at step D is YES, the control system starts the power supply to turn the heat on if it is not already on at step H. The control system then determines whether the timer has reached the maximum time period at step I. If the answer in step I is YES, the control system shuts off the power and sounds an alarm (step J). If the answer in step I is NO, the control system delays at step K and repeats this process starting at step C.

In many of embodiments described above, the timer is correlated to a threshold temperature in an on/off power control system. That is, the control system resets the timer and stops a supply of power each time the threshold temperature is sensed. However, the time to temperature can be correlated to operating parameters other than the blanket temperature sensor reading. In addition, the control system may be more sophisticated than an on/off power supply system.

For instance, in some embodiments, the control system modulates the amount of power supplied (rather than simply turning a single power type on and off). Here, the control system monitors temperature of the blanket based on input received from one or more temperature sensors and modulates the power levels accordingly. For example, as the sensed temperature approaches a desired temperature threshold, the control system can gradually or incrementally reduce the power level. As the sensed temperature falls below the desired temperature, the control system can increase the power level to increase the temperature. If the sensed temperature is far below a desired temperature threshold, the control system can increase the power level even higher than that for a temperature just below the desired temperature.

Under a modulated power control system, the control system and timer can be programmed so that if the power level does not fall below a threshold level within a desired period of time, the timer expires and the control system shuts off the power supply and/or triggers an alarm. Likewise, each time the power level does fall below the threshold level, the timer is reset. Accordingly, in such embodiments, the timer reset may be based on the power supply level and not directly on temperature.

One known power modulating control system is a PID (proportional/integral/derivative) based control system. If a PID control system is used, the control system can monitor one or more process control parameters, such as an integral control term. The control system and timer can be programmed so that if the integral control term does not reach a desired level within a desired period of time, the timer expires and the control system shuts off the power supply. Likewise, each time the integral control term reaches the desired level, the timer is reset.

In some embodiments, the temperature control is provided via thermostatic switch, such as a bi-metallic thermostat, thermally coupled to the heating element an in-line with the power supply for the heating element. In such embodiments, the switch opens, thereby cutting off current to the heating element, when the heating element and its thermally coupled switch reach a set point temperature.

In some embodiments, the flexible heating element itself may act as a temperature sensor. In such embodiments, the flexible heating element is formed of a material having a resistance that varies with temperature. The controller may determine the temperature of the flexible heating element by measuring the resistance or change in resistance in the power supply circuit. The resistance of the heating element may also be used to determine the watt density output of the heating element. Thus, the heating element resistance measurement may be used as a control parameter by the controller to control or adjust the watt density output of the blanket as desired.

In the foregoing detailed description, the invention has been described with reference to specific embodiments. However, it may be appreciated that various modifications and changes can be made without departing from the scope of the invention as set forth in the appended claims. Although embodiments of the invention are described in the context of a hospital operating room, it is contemplated that some embodiments of the invention may be used in other environments. Those embodiments of the present invention that are not intended for use in an operating environment and need not meet stringent FDA requirements for repeated used in an operating environment need not include particular features described herein (e.g., features related to precise temperature control). Thus, some of the features of preferred embodiments described herein are not necessarily included in preferred embodiments of the invention which are intended for alternative uses.

What is claimed is:

1. An electric warming blanket for warming patients during surgery and other medical procedures, comprising:
   a heating element assembly;
   a power source coupled to the heating element assembly, the power source adapted to supply power to the heating element assembly;
   a controller adapted to control the supply of power from the power source;
   a temperature sensor assembly adapted to monitor the temperature of the heating element assembly; and
   a timer operatively coupled to the controller;
   wherein the controller includes a safety feature, which comprises:
      (a) a temperature sensor assembly input to receive heating element assembly temperature information from the temperature sensor assembly, and
      (b) a controller output to reduce the supply of power to the heating element assembly if the controller determines that a time limit has elapsed before the heating element assembly temperature information received from the temperature sensor assembly indicates that the temperature of the heating element assembly meets or exceeds the threshold temperature, the time limit being less than a thermal burn injury time, wherein the timer starts when the power to the heating element assembly is turned on.

2. The blanket of claim 1, wherein the controller is adapted to reset the timer after the heating element assembly temperature meets or exceeds the threshold temperature.

3. The blanket of claim 1, wherein the timer is started when the controller starts the supply of power.

4. The blanket of claim 3, wherein the start of the supply of power occurs after the heating element assembly temperature falls below the threshold temperature.

5. The blanket of claim 1, wherein the controller is adapted to shut off the supply of power to the heating element assembly when the time limit has elapsed.

6. The blanket of claim 1, wherein the controller is adapted to prompt the power source to supply power to the heating element assembly when the heating element assembly temperature is below the threshold temperature.

7. The blanket of claim 1, wherein the controller is adapted to increase the supply of power to the heating element assembly as the heating element assembly temperature drops below the threshold temperature.

8. The blanket of claim 1, wherein the controller is adapted to reduce the supply of power to the heating element assembly as the heating element assembly temperature increases toward the threshold temperature.

9. The blanket of claim 8, wherein the controller is further adapted to reset the timer when the supply of power falls below a threshold level.

10. The blanket of claim 8, wherein the controller is a PID controller adapted to monitor an integral control term, the controller being further adapted to reset the timer when the integral control term reaches a threshold level.

11. The blanket of claim 1, wherein the power source is adapted to supply power to the heating element assembly until the heating element assembly temperature equals the threshold temperature.

12. The blanket of claim 1, wherein the threshold temperature is between 37 and 43° C.

13. The blanket of claim 1, wherein the heating element assembly has a generally uniform watt density output of less than approximately 0.5 watts/square inch.

14. The blanket of claim 1, wherein the time limit is less than about 20 minutes.

15. The blanket of claim 14, wherein the time limit is between about 5 and about 15 minutes.

16. The blanket of claim 15, wherein the time limit is about 10 minutes.

17. The blanket of claim 1, wherein the controller is adapted to trigger one or more alarms when the time limit has elapsed.

18. The blanket of claim 17, wherein the one or more alarms includes at least one of a visible alarm and an audible alarm.

19. An electric warming blanket having a safety feature for preventing thermal burn injury, the electric warming blanket comprising:
   a heating element assembly;
   a power source coupled to the heating element assembly, the power source adapted to supply power to the heating element assembly;
   a controller adapted to control the supply of power from the power source;
   a temperature sensor assembly adapted to measure a temperature of the heating element assembly and provide the temperature to the controller, the power source being adapted to supply power to the heating element assembly until the controller determines from the temperature sensor assembly that a threshold temperature is reached; and
   a timer operatively coupled to the controller, wherein the timer starts when the power to the heating element assembly is turned on, the controller being adapted to determine from the timer whether a time limit has elapsed, the controller being further adapted to (a) shut off the supply of power to the heating element assembly when the time limit has elapsed and (b) reset the timer when the heating element assembly temperature meets or exceeds the threshold temperature.

20. The blanket of claim 19, wherein the time limit is less than a thermal burn injury time.

21. The blanket of claim 20, wherein the controller is adapted to set the time limit based on whether the heating element assembly has reached a steady state operation for a period of time.

22. The blanket of claim 21, wherein the time limit is reduced once the heating element assembly has first reached a steady state operation.

23. A method of protecting a patient from thermal burn injury in connection with an electric warming blanket, the blanket for warming patients during surgery and other medical procedures, the method comprising:
- supplying power to a heating element assembly;
- measuring a temperature of the heating element assembly;
- determining whether the measured temperature reaches a threshold;
- interrupting the supply of power after the measured temperature reaches the threshold;
- timing the period of time of the supply of power, wherein timing starts when the power to the heating element assembly is turned on; and
- interrupting the supply of power when the period of time reaches a time limit if the measured temperature has not yet reached the threshold, the time limit being less than a thermal burn injury time.

24. The method of claim 23, further including resuming the supply of power to the heating element assembly after the measured temperature drops below the threshold, and restarting the timing upon the resumption of the supply of power.

25. The method of claim 23, wherein the threshold temperature is between 37 and 43° C.

26. The method of claim 23, wherein the time limit is between about 5 and about 15 minutes.

27. The method of claim 26, wherein the time limit is about 10 minutes.

28. The method of claim 23, further comprising trigger one or more alarms when the period of time reaches a time limit.

29. An electric warming blanket for warming patients during surgery and other medical procedures, comprising:
- a heating element assembly;
- a power source coupled to the heating element assembly, the power source adapted to supply power to the heating element assembly;
- a controller adapted to control the supply of power from the power source;
- a temperature sensor assembly adapted to monitor the temperature of the heating element assembly; and
- a timer operatively coupled to the controller;
- wherein the controller includes a safety feature, which comprises:
  - (a) a timer input to receive timer information from the timer, and
  - (b) a controller output to interrupt the supply of power to the heating element assembly if the controller determines that a time limit has elapsed before the power supplied to the heating element assembly has been reduced, the time limit being less than a thermal burn injury time, wherein the timer starts when the power to the heating element assembly is turned on.

* * * * *